US012788227B2

(12) United States Patent
Subasic et al.

(10) Patent No.: US 12,788,227 B2
(45) Date of Patent: Nov. 10, 2026

(54) ACTUATORS FOR MEDICAL DEVICES AND RELATED SYSTEMS

(71) Applicant: Boston Scientific Scimed, Inc., Maple Grove, MN (US)

(72) Inventors: John Subasic, Stow, MA (US); Elizabeth A. Stokley, Raleigh, NC (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 129 days.

(21) Appl. No.: 18/773,995

(22) Filed: Jul. 16, 2024

(65) Prior Publication Data

US 2025/0025025 A1 Jan. 23, 2025

Related U.S. Application Data

(60) Provisional application No. 63/513,961, filed on Jul. 17, 2023.

(51) Int. Cl.

*A61B 1/005* (2006.01)
*A61B 1/008* (2006.01)
*A61M 25/01* (2006.01)

(52) U.S. Cl.

CPC .......... *A61B 1/0052* (2013.01); *A61B 1/0051* (2013.01); *A61B 1/008* (2013.01); *A61B 1/009* (2022.02); *A61M 25/0136* (2013.01)

(58) Field of Classification Search

CPC ..... A61B 1/0052; A61B 1/009; A61B 1/0004; A61B 1/0051; A61B 1/0057; A61B 1/008; A61M 25/0147

See application file for complete search history.

(56) References Cited

U.S. PATENT DOCUMENTS

| | | | | |
|---|---|---|---|---|
| 4,718,407 | A | 1/1988 | Chikama | |
| 2015/0272425 | A1* | 10/2015 | Ueda | A61B 1/00078 600/144 |
| 2016/0227986 | A1* | 8/2016 | Yasunaga | A61B 1/0052 |
| 2022/0280021 | A1* | 9/2022 | Chu | A61B 17/221 |

* cited by examiner

*Primary Examiner* — Michael J Carey

(74) *Attorney, Agent, or Firm* — Bookoff McAndrews PLLC

(57) ABSTRACT

Medical devices and related methods are discussed, including a medical device that includes a handle with a housing and an actuator mechanism disposed within the housing. The actuator mechanism may include a biasing member and a disk rotatable between a first position and a second position, e.g., the biasing member having a first length and exerting a first distal force on the disk in the first position, and having a second length different from the first length and exerting a second distal force on the disk less than the first distal force in the second position.

20 Claims, 4 Drawing Sheets

ACTUATORS FOR MEDICAL DEVICES AND RELATED SYSTEMS

CROSS-REFERENCE TO RELATED APPLICATIONS

This application claims the benefit of priority to U.S. Provisional Application No. 63/513,961, filed on Jul. 17, 2023, which is incorporated by reference herein in its entirety.

TECHNICAL FIELD

Various aspects of the present disclosure relate generally to actuator mechanisms for medical devices. More specifically, embodiments of this disclosure relate to actuators for medical device handles that include a control assembly for providing a mechanical advantage, among other aspects.

BACKGROUND

During a medical procedure, an operator may utilize a medical device that includes a handle and a shaft extending distally therefrom. For example, the medical device may be an endoscopic medical device. The shaft of the medical device may be inserted into a working channel of an endoscope (or other scope), advanced through the working channel, and extended out of a distal opening of the working channel, at a distal tip of the endoscope. The shaft of the medical device may additionally or alternatively be inserted directly into a patient, for example, via an incision or a natural orifice. An operator may actuate the medical device using the handle of the medical device. For example, the operator may activate an actuator at the handle. In an example, the actuator may include moving a finger grip.

Activating the actuator of a medical device may require exertion of a large force. For example, during medical procedures, a medical professional operating a medical device often wraps his/her entire palm around a grip or handle portion of a medical device and utilizes one or more of his/her fingers to access or activate various actuators on the medical device. Medical professionals can experience wrist and hand discomfort resulting from holding and manipulating the handle of the device, repetitive hand adjustments to access the actuator(s), and/or activating actuator(s) on the device. In some cases, medical professionals may experience symptoms similar to those of Carpal Tunnel Syndrome, tendonitis, or De Quervain's tenosynovitis.

When a medical professional experiences fatigue or other pain in the fingers, hand, or wrist, the medical professional may take breaks from the procedure and/or shift from a primary grip position to a secondary grip position. Repeatedly reaching or contorting the fingers to access or activate various actuators on the device may increase fatigue or other pain. When a medical professional repeatedly readjusts his or her handgrip in between procedure tasks, the procedure may be prolonged and procedural tasks may be more difficult.

The systems and devices of this disclosure may rectify some of the deficiencies described above or address other aspects of the art.

SUMMARY

The present disclosure includes, for example, a medical device comprising a handle having a housing and an actuator mechanism disposed within the handle. The actuator mechanism may include a disk and a biasing member, e.g., the disk being rotatable between a first position and a second position. A proximal end of the biasing member may be coupled to the disk and a distal end of the biasing member may be coupled to the housing. According to some aspects, in the first position of the disk, the biasing member has a first length and exerts a first distal force on the disk and/or in the second position of the disk, the biasing member has a second length different from the first length and exerts a second force distal on the actuator less than the first distal force.

Any of the medical devices described herein may include any combination of the following features. The first length of the biasing member may be greater than the second length of the biasing member. In some examples, the disk includes a first protrusion on a first side of the disk and a second protrusion on a second side of the disk. An inner surface of the housing may receive the first protrusion on a first side of the handle and the second protrusion on a second side of the handle, opposite the first side. The actuator mechanism may further include a lever coupled to the disk. For example, the lever may be coupled to an outer surface of the housing of the handle. The lever may be rotatable to drive a corresponding rotation of the disk.

In some examples, the biasing member may be fixed to a proximal portion of the disk. Additionally or alternatively, the actuator mechanism may further include first and second control members each coupled to the disk. In some examples, the first control member is attached to the disk by a first coupler, the second control member is attached to the disk by a second coupler, and/or the biasing member is attached to the disk by a third coupler. The third coupler may be between the first coupler and second coupler. Movement of the disk from the first position to the second position is configured to move the first control member proximally and the second control member distally. Movement of the disk from the second position to the first position may be configured to move the first control member distally and the second control member proximally.

In some examples, the biasing member includes a spring. According to some aspects, in a third position of the disk, the biasing member has a third length and exerts a third distal force on the disk. The third distal force may be less than the first distal force. The disk may be rotatable in a first direction between the first position and the second position and/or may be rotatable in a second direction between the first position and the third position.

In some examples, the medical device further comprises a shaft coupled to the handle. The shaft may include an articulation section operably coupled to the actuator mechanism. Movement of the disk from the first position to the second position may be configured to move the articulation section of the shaft along a first plane. Further, for example, movement of the disk from the first position to a third position may be configured to move the articulation section of the shaft along a second plane transverse to, e.g., perpendicular to, the first plane.

The present disclosure also includes a medical device that includes a handle comprising a housing and an actuator mechanism disposed within the handle. The actuator mechanism may include a rotatable disk, a biasing member coupled to, and configured to exert a force on, the disk, a first control member coupled to the disk, and a second control member coupled to the disk. The handle may be configured to rotate from a first configuration to a second configuration by rotation of the disk. In the second configuration, for example, the force exerted on the disk is greater than the force exerted on the disk in the second configuration. Rotating from the first configuration to the second configuration may shorten a length of the biasing member. The actuator mechanism may include a lever coupled to the disk, e.g., the lever configured to be engaged by a user to drive rotation of the disk. In some examples, a shaft is coupled to the handle. The shaft may include an articulation section operably coupled to the actuator mechanism. Movement of the disk may be configured to control the articulation section.

The present disclosure also includes a medical device that includes a handle comprising a housing and an actuator mechanism disposed within the housing. The actuator mechanism may include a disk rotatable between a first position and a second position, a biasing member, a first control member coupled to the disk, and a second control member coupled to the disk. A proximal end of the biasing member may be coupled to the disk and a distal end of the biasing member may be coupled to an internal surface of the housing. The disk may include a first protrusion on a first side of the disk and a second protrusion on a second side of the disk. The housing may receive the first protrusion on a first side of the handle and the second protrusion on a second side of the handle opposite the first side.

BRIEF DESCRIPTION OF THE DRAWINGS

The accompanying drawings are incorporated in and constitute a part of this application. These drawings illustrate aspects of the disclosure that, together with the written descriptions herein, serve to explain this disclosure. Each drawing depicts one or more exemplary aspects according to this disclosure, as follows.

DETAILED DESCRIPTION

Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., patient). By contrast, the term "proximal" refers to a portion closest to the user when placing the device into the subject. Proximal and distal directions are labeled with arrows marked "P" and "D," respectively, throughout various figures.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Although the treatment site is discussed herein as being in the subject's gastrointestinal tract, this disclosure is not so limited, as the treatment site may be any internal lumen, organ, cavity, or other tissue within the subject. Additionally, although endoscopes are referenced herein, it will be appreciated that the disclosure encompasses any medical device having an articulable distal end portion. In some examples, the medical device has a working channel, or a lumen, extending from a proximal end to a distal end. The medical device may include a ureteroscope, duodenoscope, gastroscope, endoscopic ultrasonography ("EUS") scope, colonoscope, bronchoscope, laparoscope, arthroscope, cystoscope, aspiration scope, sheath, or catheter. In some examples, the medical device may include a handle and a shaft, extending distally from the handle. The shaft of the medical device may be inserted into a working channel of another medical device (e.g., an endoscope or other type of scope). Alternatively, the shaft of the medical device may be inserted directly into an incision, opening, or orifice of a subject.

Embodiments of the present disclosure may address one or more of the limitations in the art. The scope of the disclosure, however, is defined by the attached claims and not the ability to solve a specific problem. The present disclosure is drawn to devices and system, for decreasing a force required to deflect a portion of the medical device, among other aspects.

Figure 1:
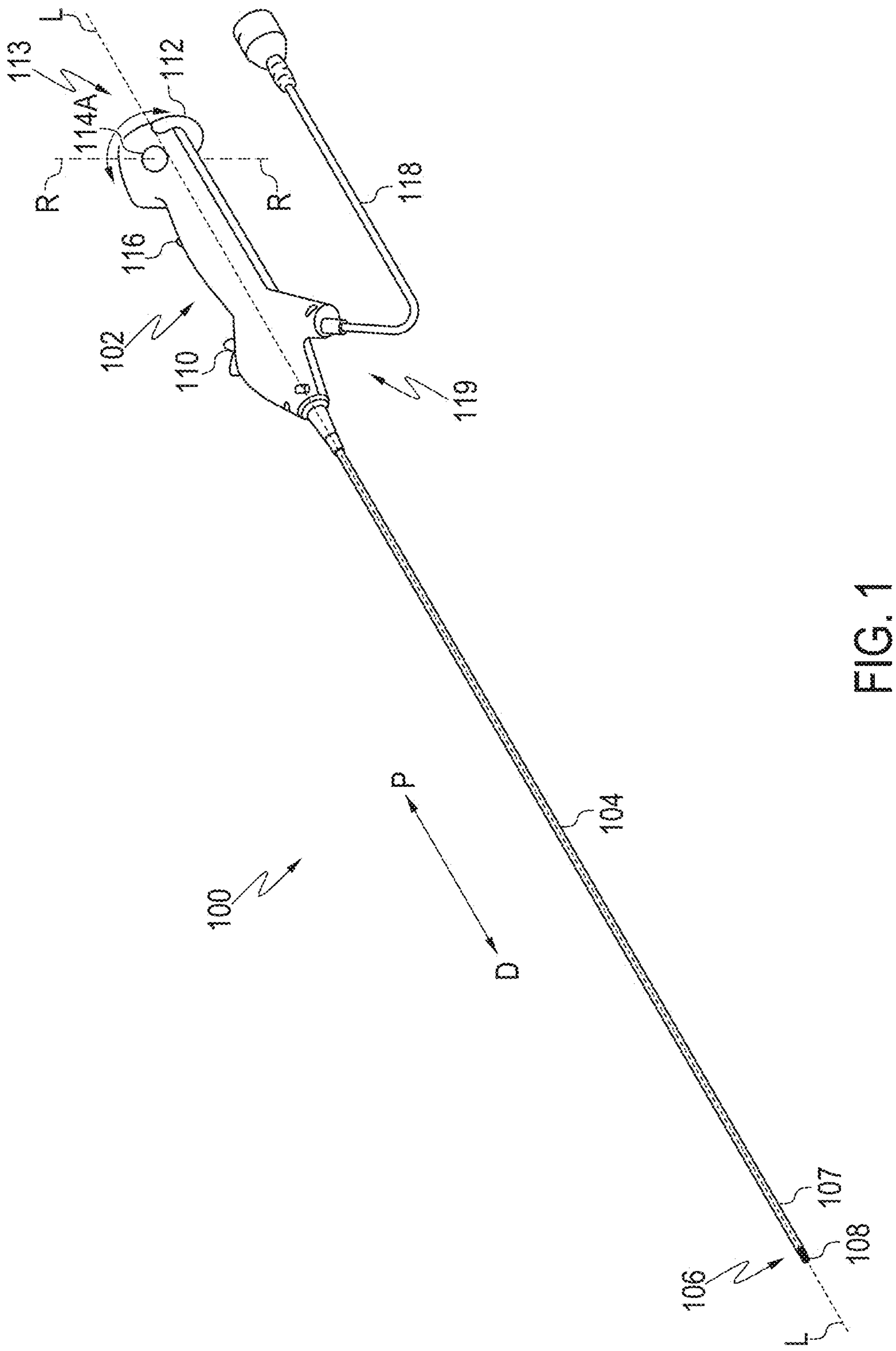
FIG. 1 depicts an exemplary medical device, according to aspects of this disclosure.

FIG. 1 depicts an exemplary medical device 100, which may include a handle 102 having a housing and an insertion portion/shaft 104 coupled to handle 102. Insertion portion 104 may be configured for insertion into a subject. In some examples, at least portions of insertion portion 104 may be rigid or inflexible. Alternatively, at least portions of insertion portion 104 may be flexible, such that insertion portion 104 may conform to a tortuous path of a subject. In further examples, insertion portion 104 may include a combination of rigid portion(s) and flexible portion(s) and/or portions of varying rigidities/flexibilities. For example, a distal portion 106 of insertion portion 104 may be more flexible than a proximal portion of insertion portion 104. A proximal end of insertion portion 104 may be coupled to a distalmost end of handle 102.

Handle 102 may be used to actuate and/or articulate the distal portion 106 of insertion portion 104. Distal portion 106 may include a bendable portion, e.g., an articulation section 107. A distalmost end 108 of distal portion 106 may include one or more imaging devices (e.g., an imager, a lens, a camera, etc.) and/or illumination devices (e.g., light-emitting diodes, fiber optics, bulbs, etc.). Distalmost end 108 may additionally or alternatively include one or more openings. The opening(s) may be in fluid communication with one or more lumens extending through insertion portion 104 and into handle 102. For example, a port 110 disposed on handle 102 may be in fluid communication with one or more openings of distalmost end 108.

One or more auxiliary devices such as, for example, a snare, a basket, a balloon, a stent delivery system, forceps, a stapler, a needle, a cautery device, a suturing device, an agent delivery system, a patch delivery system, or any other suitable medical device, may be inserted through port 110 and extend distally from the opening(s) at distalmost end 108. Additionally or alternatively, the opening(s) of distalmost end 108 may be configured to provide irrigation, suction, and/or insufflation to a treatment site. A longitudinal axis L of medical device 100 may extend along a proximal/distal direction of medical device 100.

Handle 102 may include one or more actuators, which may be activated or engaged by a user to control various aspects of medical device 100. For example, handle 102 may include a lever 112 operably coupled to an actuator mechanism within the housing of handle 102. As shown in FIG. 1, lever 112 may be disposed on a proximal portion of handle 102, for example, at or near a proximal-most end 113 of handle 102. Lever 112 may include a knob or a bar configured to be activated or engaged by a user. Lever 112 may be rotatable clockwise and counterclockwise about an axis R, for example, in the directions illustrated by the curved arrows of FIG. 1. Axis R may be substantially perpendicular to longitudinal axis L.

In some aspects of the present disclosure, axis R may extend through a first protrusion 114A and a second protrusion 114B of actuator mechanism comprising a disk 120 (see FIGS. 2, 4A, 4B) within handle 102. First protrusion 114A may be on a first side of handle 102 (e.g., a side facing out of the page), and second protrusion 114B may be on a second, opposite side of handle 102 (e.g., a side facing into the page). Second protrusion 114B is not visible in the configurations shown in FIGS. 1 and 2 but is shown in FIG. 4B, discussed below.

Lever 112 may be operably coupled (e.g., directly or indirectly) to disk 120 of the actuator mechanism. In such a way, rotation of lever 112 drives a corresponding rotation of disk 120. Accordingly, disk 120 is rotated about first protrusion 114A and second protrusion 114B. In such a way, disk 120 may be movable within handle 102. Each of first protrusion 114A and second protrusion 114B may extend completely or partially through each side of handle 102, thereby anchoring disk 120 within handle 102. Each of first protrusion 114A and second protrusion 114B (and thus disk 120 and lever 112) may be rotatable relative to the housing of handle 102, but immovable proximally or distally relative to the housing of handle 102. In some aspects, first protrusion 114A and/or second protrusion 114B may extend through handle 102 such that first protrusion 114A and/or second protrusion 114B is/are visible by a user on each side of handle 102 (i.e., the side of the housing of handle 102 facing out of the page and the side of the housing of handle 102 facing into the page).

In some examples, first protrusion 114A and second protrusion 114B are not visible by a user on both sides of the housing of handle 102. For example, first protrusion 114A may extend completely through one side of handle 102 and second protrusion 114B may extend partially through the other side of handle 102, or vice versa. In such a way, only one of first protrusion 114A or second protrusion 114B is visible on the housing of handle 102. In some examples, both of first protrusion 114A and second protrusion 114B may extend partially though each respective side of handle 102 such that neither first protrusion 114A nor second protrusion 114B is visible on either side of the housing of handle 102.

In some aspects, handle 102 may include one or more internal or external surface features that are complementarily shaped to first protrusion 114A and/or second protrusion 114B. For example, handle 102 may include features such as a through hole, a protrusion, an indentation, or any combination thereof. In such a way, the surface feature(s) of handle 102 may permit rotational movement of disk 120 relative to the housing of handle 102 and prevent axial or longitudinal movement of disk 120 relative to the housing of handle 102.

Shapes and relative sizes of lever 112, first protrusion 114A, second protrusion 114B, and/or handle 102 (e.g., the housing of handle 102) shown in the figures are merely exemplary, and other arrangements are contemplated within the scope of this disclosure.

Lever 112 may be configured for manual actuation by an operator. For example, lever 112 may be engaged by the operator's thumb and/or other fingers. Additionally or alternatively, lever 112 may be engaged robotically or via indirect contact by an operator. In some examples, lever 112 may be used to manipulate distalmost end 108 of insertion portion/shaft 104. For example, lever 112 may be coupled directly or indirectly to one or more control members 122 (shown and described in more detail with respect to FIG. 2). In such a way, rotation of lever 112 in a first direction (e.g., one of clockwise or counterclockwise) about first protrusion 114A and second protrusion 114B may articulate distalmost end 108 in a first direction (e.g., up and down along a first plane). Rotation of lever 112 in a second direction (e.g., the other of counterclockwise or clockwise) about first protrusion 114A and second protrusion 114B may articulate distalmost end 108 in a second direction, different from the first direction (e.g., right and left along a second plane perpendicular to the first plane). With lever 112 in a neutral position (e.g., before an operator engages lever 112), distalmost end 108 may be oriented in a straight configuration, e.g., extending along longitudinal axis L.

Additionally or alternatively, moving lever 112 in the first direction may actuate or activate distalmost end 108, and moving lever 112 in the second direction may deactivate distalmost end 108. For example, moving lever 112 in the first direction may open an aperture of distalmost end 108, and moving lever 112 in the second direction may close the aperture of distalmost end 108. In further examples, moving lever 112 in the first or second direction may extend, retract, deform, or otherwise manipulate distalmost end 108 relative to a starting position of distalmost end 108 in the neutral position.

Handle 102 may include one or more other actuators in the form of control(s) 116 (e.g., buttons, switches, knobs, etc.). Control(s) 116 may be engaged by a user, the control(s) 116 being configured to control one or more aspects of medical device 100. For example, control(s) 116 may be configured to power an imaging device and/or an illumination device/light source of distalmost end 108, provide suction and/or irrigation at distalmost end 108, capture or take video and/or still images from an imaging device at distalmost end 108, lock lever 112 in a position, adjust an intensity of an illumination device/light source at distalmost end 108, etc.

A cable 118 (e.g., an umbilicus) may be fixedly or removably coupled to handle 102. For example, cable 118 may be coupled to a distal portion 119 of handle 102. Cable 118 may extend from handle 102, for example, to one or more auxiliary devices. The one or more auxiliary devices may include, for example, a control system, an imaging system, a power supply, a fluid supply, a suction/vacuum source, a display, etc. In some examples, cable 118 may be configured to supply power to an imaging device and/or illumination device/light source of distalmost end 108 and transmit electrical signals from the imaging device of distalmost end 108 to the auxiliary device(s).

During use, handle 102 may remain outside of a subject's body such that handle 102 may be directly or indirectly manipulated by the operator. Engaging lever 112 (e.g., moving lever 112 in a first and/or second direction) may rotate disk 120 (shown in FIG. 2) about first protrusion 114A and second protrusion 114B, thus controlling one or more aspects of distal portion 106 of medical device 100. For example, lever 112 may be used to control articulation section 107 of distal portion 106 of insertion portion 104, articulate an end effector, open/close jaws or blades, extend/retract a snare, a needle, a basket, or other device, deploy a medical instrument, staple tissue, cut tissue, and/or perform any other action during a medical procedure. Insertion portion 104 of the medical device 100 may pass through one or more tortuous body lumens when used alone or along with an endoscope or other type of scope. Accessory devices may be inserted through port 110 of handle 102, e.g., through a lumen of insertion portion/shaft 104, and extend distally past distalmost end 108 of distal portion 106.

Figure 2:
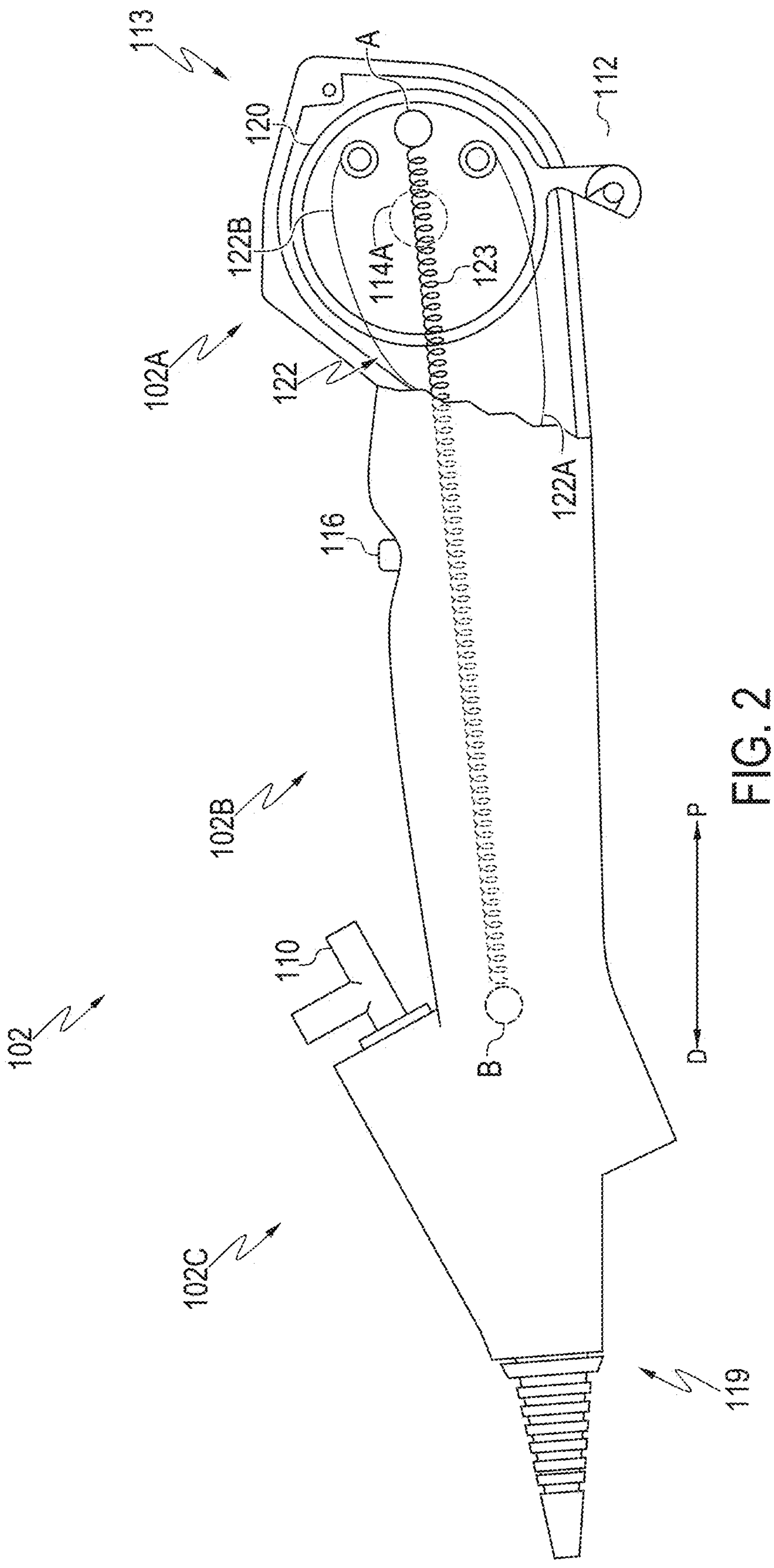
FIG. 2 depicts a partial cross section of the medical device of FIG. 1, according to aspects of this disclosure.

FIG. 2 illustrates a partial cross-section of handle 102. Handle 102 comprises a proximal portion 102A, a distal portion 102C, and a central portion 102B. Proximal portion 102A may form proximal-most end 113 of handle 102, and distal portion 102C may form distal portion 119 of handle 102. Central portion 102B may be distal to proximal portion 102A and proximal to distal portion 102C.

In some examples, proximal portion 102A and/or distal portion 102C may have a greater cross-sectional dimension (e.g., width) than that of central portion 102B. For example, proximal portion 102A and/or distal portion 102C may be wider than central portion 102B. In some examples, central portion 102B may be formed to facilitate the operator's grip of handle 102. Proximal portion 102A, central portion 102B, and/or distal portion 102C may include one or more additional features to facilitate an operator's grip on handle 102. For example, one or more additional features on proximal portion 102A, central portion 102B, and/or distal portion 102C may include surface features such as raised features and/or indented features, and/or may include a texture such as rough features and/or smooth features, or any combination thereof, to facilitate a user's grip on handle 102.

As previously discussed, shapes and relative sizes of handle 102 (e.g., the housing of handle 102) shown in the figures are merely exemplary, and other arrangements are contemplated within the scope of this disclosure. For example, in other examples, each of proximal portion 102A, central portion 102B, and distal portion 102C may have a same or similar cross-sectional dimension (e.g., width). In such a way, handle 102 may have the same cross-sectional width along substantially all of the longitudinal length of handle 102. For example, proximal portion 102A may have the same width as central portion 102B and distal portion 102C.

Disk 120 may be disposed or contained within the housing of handle 102, e.g., within proximal portion 102A of handle 102. Lever 112 may be coupled (e.g., directly or indirectly) to disk 120, for example, via a mechanical fastener (e.g., a screw, a press-fit, a bolt, a weld, a rivet, etc.). In some examples, lever 112 is integrally formed with disk 120. For example, disk 120 may be a single molded component comprising lever 112. Lever 112 may be external to the housing of handle 102 while disk 120 may be at least partially contained within the housing of handle 102. As previously discussed, disk 120 may be coupled to first protrusion 114A, illustrated by dashed circles in FIG. 2 to allow for clearer representation of disk 120 and other features of the actuator mechanism.

A proximal end of each of one or more control members 122 (e.g., a first control member 122A and a second control member 122B) may be coupled (e.g., directly or indirectly) to disk 120. As described in further detail below with respect to FIGS. 4A and 4B, each of the one or more control members 122 may be coupled to a proximal portion of disk 120, proximal to first protrusion 114A and second protrusion 114B. The proximal end of each of the one or more control member(s) 122 may be coupled to disk 120 via one or more mechanical fasteners (e.g., screws, bolts, ferrules, etc.), adhesive, weld, or any other suitable material.

A distal end each control member 122 may be similarly coupled (e.g., directly or indirectly) to distal portion 106 (shown in FIG. 1) of insertion portion/shaft 104. For example, each control member 122 may extend distally through handle 102 and insertion portion 104 to distal portion 106 (shown in FIG. 1). Accordingly, as lever 112 is moved in the first and/or second directions (e.g., rotated clockwise or counterclockwise), each of control member(s) 122 may be translated proximally or distally. For example, as lever 112 rotates clockwise such that disk 120 rotates about first protrusion 114A and second protrusion 114B, first control member 122A is translated distally and second control member 122B is translated proximally. The distal translation of first control member 122A and proximal translation of second control member 122B may in turn activate or otherwise engage distal portion 106, as previously described with respect to FIG. 1. For example, the distal translation of first control member 122A and the proximal translation of second control member 122B may bend articulation section 107 (shown in FIG. 1) in a first direction.

Furthermore, as lever 112 is rotated counterclockwise, disk 120 rotates such that first control member 122A is translated proximally and second control member 122B is translated distally. The proximal translation of first control member 122A and the distal translation of second control member 122B similarly may activate or otherwise engage distal portion 106. For example, the proximal translation of first control member 122A and the distal translation of second control member 122B may bend articulation section 107 (shown in FIG. 1) in a second direction.

Medical device 100 may further include a biasing member 123 (e.g., a spring, a coil, an elastic member, etc.) disposed within handle 102, e.g., as part of the actuator mechanism. A proximal end of biasing member 123 may be fixed to a proximal portion of disk 120 at a point A, for example, proximal to first protrusion 114A and second protrusion 114B. The proximal end of biasing member 123 may be fixed to point A via a mechanical fastener (e.g., a screw, a setscrew, a bolt, a rivet, etc.) and/or the proximal end of biasing member may be molded, overmolded, welded, or otherwise fixed to disk 120. A distal end of biasing member 123 may be fixed within central portion 102B or distal portion 102C of handle 102 at a point B. For example, the distal end of biasing member 123 may be fixed to an internal surface or feature of handle 102 at point B. Although not shown, the internal surface of handle 102 may include a feature (e.g., protrusion or an indentation) to which the distal end of biasing member 123 may be fixed. The distal end of biasing member 123 may be fixed to handle 102, for example, via a mechanical fastener (e.g., a screw, a setscrew, a bolt, a rivet, etc.), adhesive, or by way of being molded into, overmolded with, or welded to an internal surface of handle 102. The location of point B is merely exemplary in FIG. 2. For example, point B may be positioned more distally or more proximally within handle 102 and/or point B may be positioned lower (e.g., closer to the bottom of the page) or higher (e.g., closer to the top of the page) within handle 102. The location of point B may be selected based on the desired tension to be applied to disk 120 by biasing member 123. For example, a more proximal placement may result in less tension forces being applied to disk 120 by biasing member 123. Alternatively, a more distal placement may result in more tension forces being applied to disk 120 by biasing member 123.

Biasing member 123 may be configured to at least partially balance the forces being applied to disk 120 by each control member 122, thereby reducing strain on the user/operator (e.g., a medical professional). As described in further detail below, the force sufficient to move lever 112 in the first and second directions may be reduced, and/or a smoother deflection experience may be created with biasing member 123.

Figure 3:
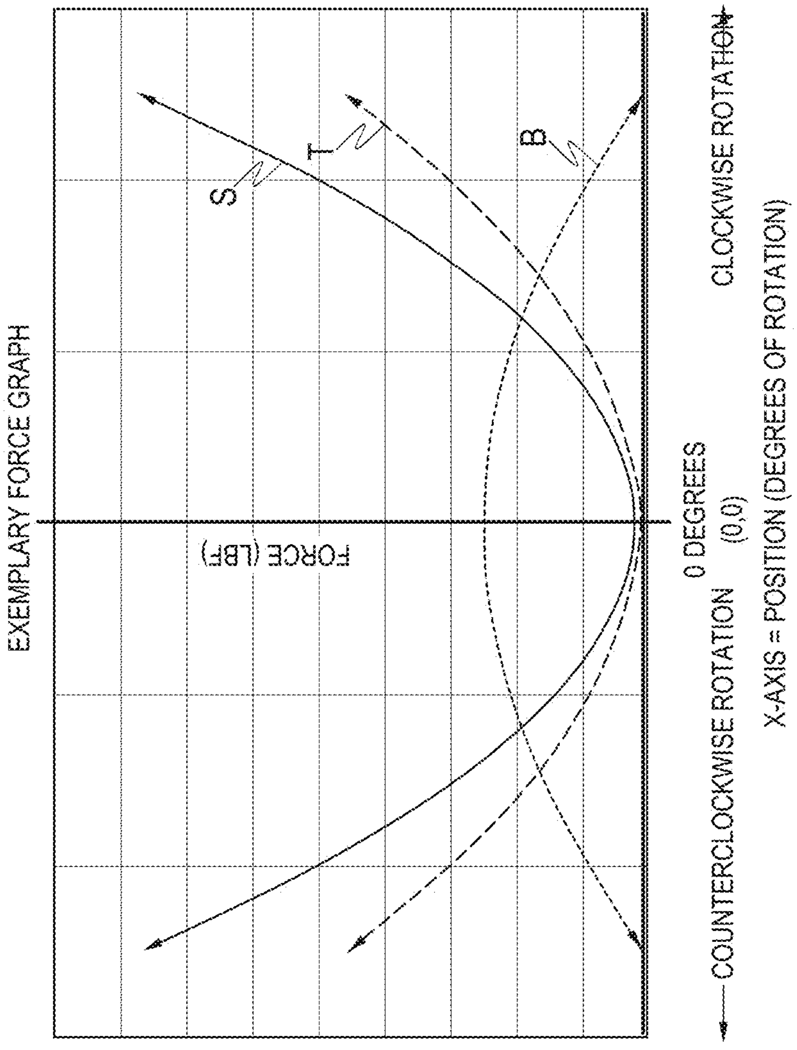
FIG. 3 illustrates an exemplary force graph, according to aspects of this disclosure.

FIG. 3 illustrates an exemplary graph of the forces sufficient to move lever 112 in the first and second directions without biasing member 123 (solid line S). The forces of biasing member 123 acting on disk 120 are illustrated by dotted line B. Dashed line T illustrates the resulting forces sufficient to move lever 112 after implementation of biasing member 123. The Y-axis of the graph represents the force (e.g., units of pound-force), and the X-axis represents the positions in degrees of lever 112 relative to the neutral position (e.g., zero degrees of rotation) and the forces of biasing member 123 acting upon disk 120 when disk 120 is rotated in the first or second directions, as described above. For example, along the positive X-axis, lever 112 may be moved in the first direction (e.g., clockwise), and along the negative X-axis, lever 112 may be moved in the second direction (e.g., counterclockwise).

As illustrated by line T of FIG. 3, the force sufficient to move lever 112 in the first or second direction may decrease with the implementation of biasing member 123. In such a way, biasing member 123 may assist in reducing the force sufficient to move lever 112 in the first and/or second directions, thereby facilitating use by a medical professional. For example, when lever 112 is in the neutral position, biasing member 123 may be more tensioned than when the disk 120 is rotated in the first or second directions (e.g., clockwise or counterclockwise). Biasing member 123 may have a first length in the neutral position, in which biasing member 123 may apply a maximum distal force on disk 120. The distal force acting on disk 120 by biasing member 123 may assist in maintaining disk 120 in the neutral position, e.g., without intervention by a user.

As disk 120 is rotated in the first and/or second directions, biasing member 123 may become less extended, thus tension in biasing member 123 is reduced. For example, as disk 120 is rotated in the first and/or second directions, biasing member 123 may shorten such that biasing member 123 has a second length less than the first length of the biasing member 123 in the neutral position. Accordingly, as disk 120 approaches the maximum angle of rotation in the first or second directions, the distal forces being exerted on disk 120 by biasing member 123 may decrease. Thus, biasing member 123 may effectively decrease the force sufficient to move lever 112.

The distal forces being applied to disk 120 by biasing member 123 may further assist in biasing disk 120 in the first or second direction. For example, when disk 120 is rotated such that disk 120 is no longer in the neutral position, biasing member 123 may exert tension forces on disk 120, thus assisting in rotating disk 120 towards the maximum angle of rotation in the first and/or second directions. The distal forces being applied by biasing member 123 may reduce the force sufficient to move lever 112 and thereby rotate disk 120. For example, because biasing member 123 is applying a distal force on disk 120, the operator may apply less force on lever 112 while still achieving the desired articulation of distal portion 106 via rotation of disk 120. In such a way, biasing member 123 may assist in rotating disk 120, and, thus, deflection of distal portion 106 of insertion portion/shaft 104 may be achieved.

Furthermore, because disk 120 may be anchored on both sides of handle 102, as described above, off-angle torque forces associated with forces applied by the operator and/or other features of medical device 100 may be reduced, thus further reducing the forces for rotating disk 120. In some examples, the off-angle torque forces may be caused by the operator exerting an off-angle force against lever 112. The off-angle force applied to lever 112 may cause disk 120 to become off-centered or offset from a longitudinal axis of disk 120 parallel to longitudinal axis L of medical device 100. Additionally or alternatively, off-angle torque forces may be associated with disk 120 and biasing member 123 being arranged in different planes by way of design.

Figure 4A:
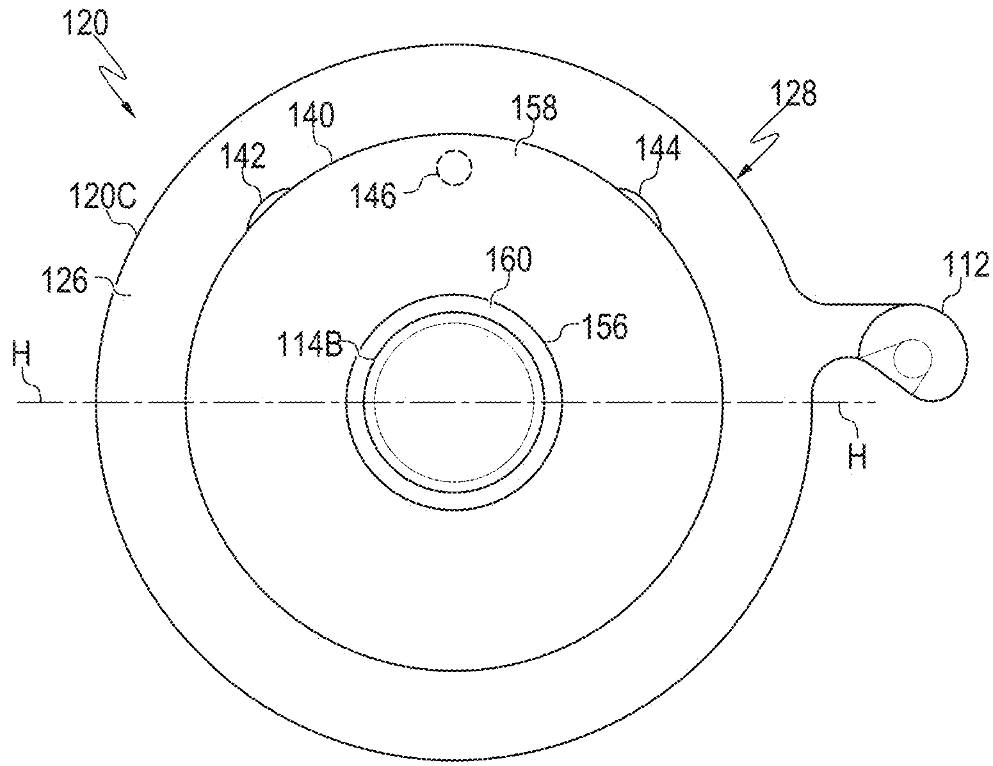
FIGS. 4A and 4B depict a portion of a control assembly of the medical device of FIGS. 1 and 2, according to aspects of this disclosure.
Figure 4B:
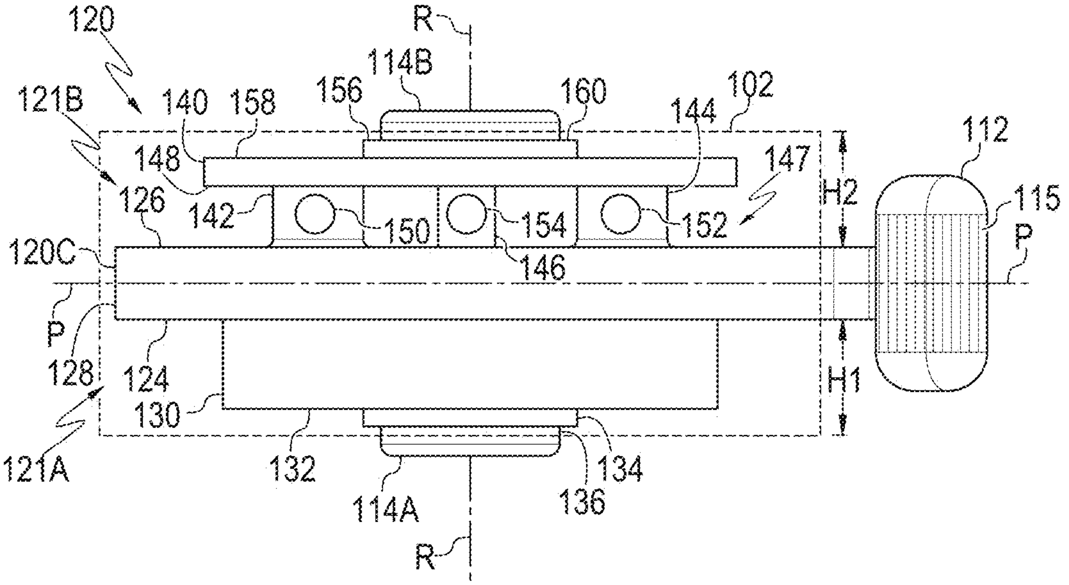

FIGS. 4A and 4B illustrate a side view (FIG. 4A) and a top view (FIG. 4B) of disk 120. Disk 120 may be formed of a single component (e.g., a single molded component) or two or more components coupled together. Additionally or alternatively, disk 120 may comprise a single material or two or more materials. The material(s) may be lubricious and/or disk 120 may be coated with a lubricious material. The lubricious material(s) may facilitate rotation of disk 120, for example, within handle 102. As previously described, disk 120 is part of an actuator or actuator mechanism that also includes lever 112, first protrusion 114A, and second protrusion 114B.

A plane P extending through a midline of disk 120 may divide disk 120 into two sides: first side 121A and second side 121B. First protrusion 114A and second protrusion 114B may extend outward from first side 121A and second side 121B, respectively. Additionally, lever 112 may extend radially outward from disk 120. Lever 112 may include one or more surface features 115 (e.g., protrusions, indentations, grips, etc.) to facilitate the operator's grip on lever 112. One or more portions of disk 120 may be hollow and/or solid.

Disk 120 may include a first cylindrical portion 120C. First cylindrical portion 120C may include a first wall 124, a second wall 126, and a third wall 128. First wall 124 may be parallel to second wall 126. Third wall 128 may extend between first wall 124 and second wall 126. Lever 112 may extend radially outward from third wall 128. In some examples, each of first wall 124, second wall 126, and third wall 128 may be substantially flat or planar.

In some examples, first wall 124 and/or second wall 126 may include one or more protrusions and/or indentations configured to limit rotational movement of disk 120 relative to the housing of handle 102. For example, the protrusions and/or indentations may abut or mate with corresponding features on an inner surface of the housing of handle 102 to inhibit or prevent rotation of disk 120 past a predetermined position. In such a way, the feature(s) may serve as a stop.

In some embodiments, third wall 128 may be curved, for example, similar to a wheel or disc (outwardly curved) or a guide wheel (inwardly curved). Handle 102 may include complementary features, for example, to accommodate a curvature of third wall 128. For example, handle 102 may include an inwardly-curved feature to mate with or abut an outwardly-curved surface of third wall 128. The inwardly-curved feature of handle 102 may assist with aligning disk 120 within handle 102. Similarly, handle 102 may include an outwardly-curved feature to mate with or abut an inwardly-curved surface of third wall 128 of disk 120. In such an example, the outwardly-curved feature of handle 102 may assist with aligning disk 120 within handle 102. Handle 102 (e.g., the housing of handle 102) may include additional features to assist with maintaining the position of disk 120 within handle 102 or aligning disk 120 within handle 102.

First side 121A of disk 120 may include a first feature 130 extending outward from first wall 124 of first cylindrical portion 120C, for example, along axis R. For example, a center axis of first feature 130 may be aligned with a center axis of first cylindrical portion 120C such that first feature 130 is concentric to first cylindrical portion 120C. First feature 130 may be similarly or complementarily shaped to first cylindrical portion 120C. For example, first feature 130 may be cylindrically shaped, similar to first cylindrical portion 120C. Alternatively, first feature 130 may be square or rectangular. A diameter of first feature 130 may be smaller than a diameter of first cylindrical portion 120C. A height of first feature 130 (e.g., a dimension measured from first wall 124 of first cylindrical portion 120C to an outer wall 132 of first feature 130) may be equal to, less than, or greater than a height of first cylindrical portion 120C (e.g., a dimension measured from first wall 124 to second wall 126 of first cylindrical portion 120C). First feature 130 may be hollow or solid. First feature 130 may be sized and/or shaped to accommodate for internal features or contours of handle 102. For example, first feature 130 may be sized and/or shaped to reduce the size of handle 102.

A second feature 134 may extend from an outer wall of 132 of first feature 130, and first protrusion 114A may extend outward from an outer wall 136 of second feature 134. Similar to first feature 130, a center axis of second feature 134 and first protrusion 114A may be aligned with a center axis of first feature 130 and axis R such that second feature 134 and first protrusion 114A are concentric to one another and to first feature 130. Second feature 134 may be similarly or complementarily shaped to first feature 130. First protrusion 114A may be similarly shaped to second feature 134.

Second feature 134 and/or first protrusion 114A may have any or all of the same characteristics of first feature 130, described above. For example, second feature 134 and/or first protrusion 114A may be cylindrically shaped, similar to first feature 130. Alternatively, second feature 134 may be square or rectangular. A diameter of second feature 134 may be smaller than a diameter of first feature 130 and/or first cylindrical portion 120C. A diameter of first protrusion 114A may be smaller than a diameter of second feature 134. A height of second feature 134 (e.g., a dimension measured from outer wall 132 of first feature 130 to outer wall 136 of second feature 134) may be less than a height of first feature 130 (e.g., a dimension measured from first wall 124 of first cylindrical portion 120C to outer wall 132 of first feature 130). Alternatively, the height of second feature 134 may be greater than or equal to the height of first feature 130. Additionally or alternatively, a height of first protrusion 114A may be smaller than, greater than, or equal to the height of second feature 134 and/or the height of first feature 130.

First side 121A of disk 120 may include one or more additional elements between second feature 134 and first protrusion 114A. The additional element(s) may incrementally decrease in diameter. Additionally, the additional element(s) may each vary in height or have the same height. For example, an additional element (not shown) abutting outer wall 136 of second feature 134 may have a smaller diameter and a smaller height than that of second feature 134. Alternatively, third feature (not shown) may have a smaller diameter and a greater height than that of second feature 134. Many other configurations are also considered.

Optionally, first feature 130 and/or second feature 134 may be omitted such that first protrusion 114A may extend directly outward from first wall 124 of first cylindrical portion 120C or from outer wall 132 of first feature 130.

Second side 121B of disk 120 may include a plate 140. A first coupler 142, a second coupler 144, and a third coupler 146 may extend outward from second wall 126, for example, away from a central plane P and between first cylindrical portion 120C and plate 140. For example, each of first coupler 142, second coupler 144, and third coupler 146 may extend between second wall 126 and an inner wall 148 of plate 140. In such a way, first coupler 142, second coupler 144, and third coupler 146 separate first cylindrical portion 120C and plate 140 to create a gap 147. First coupler 142 and second coupler 144 may each be configured to receive first control member 122A and second control member 122B, respectively. First control member 122A, second control member 122B, and biasing member 123 extend between first cylindrical portion 120C and plate 140, for example, through gap 147. In some examples, plate 140 may be configured to provide a barrier between first control member 122A, second control member 122B, and biasing member 123 and other aspects of handle 102. For example, plate 140 may assist in preventing first control member 122A, second control member 122B, and biasing member 123 from becoming entangled with or snagging internal features of handle 102 during use.

Each of first coupler 142, second coupler 144, and third coupler 146 may be columnar. Third coupler 146 may be disposed between first coupler 142 and second coupler 144. In some examples, portions of first coupler 142 and/or second coupler 144 may extend beyond an outer edge or circumference of plate 140. In some examples, first coupler 142, second coupler 144, and third coupler 146 may be generally triangularly oriented relative to one another as shown, e.g., in FIGS. 2 and 4A (wherein third coupler 146 forms an apex proximal to apices formed by first coupler 142 and second coupler 144). Other arrangements are contemplated herein.

First coupler 142 and second coupler 144 may be configured to receive first control member 122A and second control member 122B (see FIG. 2), respectively. In some examples, first control member 122A may be coupled to first coupler 142 and second control member 122B may be coupled to second coupler 144. For example, first control member 122A and second control member 122B may be wrapped, tied, molded into, or otherwise coupled to, first coupler 142 and second coupler 144, respectively. In some examples, first coupler 142 may include a first through hole 150 and/or second coupler 144 may include a second through hole 152. First control member 122A and second control member 122B may extend through first through hole 150 and/or second through hole 152, respectively. Additionally or alternatively, each of first through hole 150 and second through hole 152 may be sized and/or shaped to receive the proximal ends of one or both of first control member 122A and second control member 122B. In some examples, each of first through hole 150 and second through hole 152 may be appropriately sized and/or shaped to receive a ferrule coupled to the proximal ends of each of first control member 122A and second control member 122B.

Third coupler 146 may be configured to receive biasing member 123 (shown in FIG. 2). In some examples, biasing member 123 may extend between first coupler 142 and second coupler 144 and connect to third coupler 146. For example, biasing member 123 may be wrapped, tied, molded into, or otherwise coupled to third coupler 146.

Alternatively, third coupler 146 may include a third through hole 154. Third through hole 154 may be sized and/or shaped to receive a proximal end of biasing member 123. For example, the proximal end of biasing member 123 may extend through third through hole. A center axis of third coupler 146 may be aligned with point A, shown in FIG. 2.

In some examples, one or more of first coupler 142, second coupler 144, or third coupler 146 may be offset from each other or one another. In an exemplary configuration, an axis between a center point of first coupler 142 and a center point of second coupler 144 does not intersect an axis through a center point of third coupler 146. Optionally, first coupler 142 and second coupler 144 may extend in parallel planes. In some examples, each of first coupler 142, second coupler 144, and third coupler 146 may be arranged such that all couplers are disposed on or proximate an upper portion or a lower portion of second side 121B of disk 120. For example, each of first coupler 142, second coupler 144, and third coupler 146 may be disposed above or on a first side of a horizontal or transverse plane H of disk 120.

A center axis of plate 140 may be aligned with a center axis of first cylindrical portion 120C such that plate 140 is concentric to first cylindrical portion 120C. Plate 140 may be similarly or complementarily shaped to first cylindrical portion 120C. For example, plate 140 may be cylindrically shaped, similar to first cylindrical portion 120C. A diameter of plate 140 may be smaller than a diameter of first cylindrical portion 120C. In some embodiments, a diameter of plate 140 may be equal to the diameter of first feature 130, discussed above. In some configurations, a diameter of plate 140 may be smaller than or greater than the diameter of first feature 130.

A fourth feature 156 may extend from an outer wall of 158 of plate 140, and second protrusion 114B may extend outward from an outer wall 160 of fourth feature 156. Similar to plate 140, a center axis of fourth feature 156 and second protrusion 114B may be aligned with a center axis of first cylindrical portion 120C and axis R. In such a way, fourth feature 156 and second protrusion 114B may be concentric to one another and to first cylindrical portion 120C. Fourth feature 156 may be similarly or complementarily shaped to plate 140. Second protrusion 114B may be similarly shaped to fourth feature 156. For example, fourth feature 156 and/or second protrusion 114B may be cylindrically shaped, similar to plate 140. A diameter of fourth feature 156 may be smaller than a diameter of plate 140. A diameter of second protrusion 114B may be smaller than a diameter of plate 140.

A height of fourth feature 156 (e.g., a dimension measured from outer wall 158 of plate 140 to outer wall 160 of fourth feature 156) may be less than a height of plate 140 (e.g., a dimension measured from inner wall 148 of plate 140 to outer wall 158 of plate 140). Alternatively, the height of fourth feature 156 may be greater than or equal to the height of plate 140. Additionally or alternatively, a height of second protrusion 114B may be smaller than, greater than, or equal to the height of plate 140 and/or the height of fourth feature 156.

In some examples, first side 121A and second side 121B may be mirror images of each another. For example, second side 121B of disk 120 may have each of the features described above with respect to first side 121A (e.g., first feature 130, second feature 134, etc.). Alternatively, first side 121A of disk 120 may have each of the features described above with respect to second side 121B (e.g., plate 140, fourth feature 156, first coupler 142, second coupler 144, third coupler 146, etc.). Having the same features on each side of disk 120 may assist in reducing complexity and/or cost of manufacturing disk 120.

As previously discussed, disk 120 may be disposed within the housing of handle 102. Handle 102 is shown in FIG. 4B as a dashed square box for simplicity; see also FIGS. 1 and 2. Handle 102 may include one or more openings, notches, indentations, etc. configured to receive each of first protrusion 114A and second protrusion 114B. In some examples, each of first protrusion 114A and second protrusion 114B may extend beyond the housing of handle 102 (e.g., an outermost surface of handle 102).

A first dimension H1 may be measured from first wall 124 to handle 102 on first side 121A of disk 120. A second dimension H2 may be measured from second wall 126 to handle 102 on second side 121B of disk 120. First dimension H1 may be equal to second dimension H2. In such a way, disk 120 may be centered within handle 102. Centering disk 120 within handle 102 may assist in preventing disk 120 from becoming off-centered within handle 102 and/or preventing generation of off-angle forces.

While principles of the disclosure are described herein with reference to illustrative aspects for particular medical procedures, the disclosure is not limited thereto. Those having ordinary skill in the art and access to the teachings provided herein will recognize additional modifications, applications, aspects, and substitution of equivalents all fall in the scope of the aspects described herein. Accordingly, the disclosure is not to be considered as limited by the foregoing description.

We claim:

1. A medical device comprising:

a handle comprising a housing and an actuator mechanism disposed within the housing, wherein the actuator mechanism includes:

a disk rotatable between a first position and a second position; and a biasing member, wherein a proximal end of the biasing member is coupled to the disk and a distal end of the biasing member is coupled to a portion of the housing distal to a distalmost end of the disk, wherein, in the first position of the disk, the biasing member has a first length and exerts a first distal force on the disk; and wherein, in the second position of the disk, the biasing member has a second length different from the first length and exerts a second distal force on the disk less than the first distal force.

2. The medical device of claim 1, wherein the first length of the biasing member is greater than the second length of the biasing member.

3. The medical device of claim 1, wherein the disk includes a first protrusion on a first side of the disk and a second protrusion on a second side of the disk.

4. The medical device of claim 3, wherein an inner surface of the housing receives the first protrusion on a first side of the handle and the second protrusion on a second side of the handle opposite the first side.

5. The medical device of claim 1, wherein the actuator mechanism further includes a lever coupled to the disk.

6. The medical device of claim 5, wherein the lever is coupled to an outer surface of the housing of the handle, the lever being rotatable to drive a corresponding rotation of the disk.

7. The medical device of claim 1, wherein the proximal end of the biasing member is fixed to a proximal portion of the disk.

8. The medical device of claim 1, wherein the actuator mechanism further comprises first and second control members each coupled to the disk.

9. The medical device of claim 8, wherein the first control member is attached to the disk by a first coupler, the second control member is attached to the disk by a second coupler, and the biasing member is attached to the disk by a third coupler, and wherein the third coupler is between the first coupler and second coupler.

10. The medical device of claim 8, wherein movement of the disk from the first position to the second position is configured to move the first control member proximally and the second control member distally, and wherein movement of the disk from the second position to the first position is configured to move the first control member distally and the second control member proximally.

11. The medical device of claim 1, wherein the biasing member includes a spring.

12. The medical device of claim 1, wherein, in a third position of the disk, the biasing member has a third length and exerts a third distal force on the disk, wherein the third distal force is less than the first distal force.

13. The medical device of claim 12, wherein the disk is rotatable in a first direction between the first position and the second position, and rotatable in a second direction between the first position and the third position.

14. The medical device of claim 1, wherein the medical device further comprises a shaft coupled to the handle, the shaft comprising an articulation section operably coupled to the actuator mechanism.

15. The medical device of claim 14, wherein movement of the disk from the first position to the second position is configured to move the articulation section of the shaft along a first plane, and movement of the disk from the first position to a third position is configured to move the articulation section of the shaft along a second plane perpendicular to the first plane.

16. A medical device comprising:

a handle comprising a housing and an actuator mechanism disposed within the housing, wherein the actuator mechanism includes:

a rotatable disk;

a biasing member coupled to the disk and configured to exert a force on the disk along a central longitudinal axis of the handle;

a first control member coupled to the disk; and a second control member coupled to the disk;

wherein the handle is configured to rotate from a first configuration to a second configuration by rotation of the disk, and wherein, in the second configuration, the force exerted on the disk is greater than the force exerted on the disk in the first configuration.

17. The medical device of claim 16, wherein rotating from the first configuration to the second configuration shortens a length of the biasing member.

18. The medical device of claim 16, wherein the actuator mechanism further includes a lever coupled to the disk, the lever configured to be engaged by a user to drive rotation of the disk.

19. The medical device of claim 16, further comprising a shaft coupled to the handle, the shaft comprising an articulation section operably coupled to the actuator mechanism, wherein movement of the disk is configured to control the articulation section.

20. A medical device comprising:

a handle comprising a housing and an actuator mechanism disposed within the housing, wherein the actuator mechanism includes:

a disk rotatable between a first position and a second position;

a biasing member, wherein a proximal end of the biasing member is coupled to the disk and a distal end of the biasing member is coupled to an internal surface of the housing distal of a distalmost end of the disk;

a first control member coupled to the disk; and a second control member coupled to the disk;

wherein the disk includes a first protrusion on a first side of the disk and a second protrusion on a second side of the disk, wherein the housing receives the first protrusion on a first side of the handle and the second protrusion on a second side of the handle opposite the first side.

* * * * *